(12) United States Patent
Ostrowski et al.

(10) Patent No.: US 8,420,405 B2
(45) Date of Patent: Apr. 16, 2013

(54) CARBON DIOXIDE DETECTOR HAVING BOROSILICATE SUBSTRATE

(75) Inventors: Rafael Ostrowski, Pittsburg, CA (US); Martin Debreczeny, Danville, CA (US)

(73) Assignee: Covidien LP, Mansfield, MA (US)

( * ) Notice: Subject to any disclaimer, the term of this patent is extended or adjusted under 35 U.S.C. 154(b) by 1946 days.

(21) Appl. No.: 11/526,369

(22) Filed: Sep. 25, 2006

(65) Prior Publication Data
US 2008/0083265 A1  Apr. 10, 2008

(51) Int. Cl.
*G01N 21/77* (2006.01)

(52) U.S. Cl.
USPC ........... 436/169; 422/400; 422/401; 422/421; 422/422; 422/423; 422/424; 422/425; 422/426; 422/427; 422/428; 422/429; 422/68.1; 422/82.05; 422/82.06; 422/420; 436/164; 436/170

(58) Field of Classification Search ........... 422/56, 422/57, 58, 400, 401, 420, 421, 422, 423, 422/424, 425, 426, 427, 428, 429, 68.1, 82.05, 422/82.06; 436/164, 169, 170; 435/13, 283.1, 435/287.1, 287.7, 287.8, 287.9, 288.7
See application file for complete search history.

(56) References Cited

U.S. PATENT DOCUMENTS

| | | | |
|---|---|---|---|
| 2,136,236 A | 11/1938 | Draper |
| 2,638,096 A | 5/1953 | Waldhaus |
| 2,880,072 A | 3/1959 | Grosskopf |
| 2,890,177 A | 6/1959 | Kilmer |
| 2,904,033 A | 9/1959 | Shane |
| 3,067,015 A | 12/1962 | Lawdermilt |
| 3,068,073 A | 12/1962 | Stanford |
| 3,113,842 A | 12/1963 | Udall |
| 3,114,610 A | 12/1963 | Gafford et al. |
| 3,238,020 A | 3/1966 | Eiseman |
| 3,363,833 A | 1/1968 | Laerdal |
| 3,373,735 A | 3/1968 | Gallagher |

(Continued)

FOREIGN PATENT DOCUMENTS

| | | |
|---|---|---|
| DE | 1 007 525 | 5/1957 |
| EP | 0410851 | 1/1991 |

(Continued)

OTHER PUBLICATIONS

Current Projects CapnoProbe™ SL Monitoring System posted on the company's web site; Optical Sensors Incorporated | Projects . . . http://64.226.16.15/projects.htm Copyright 2003.

(Continued)

*Primary Examiner* — Dennis M White (57) ABSTRACT

The present disclosure relates to a carbon dioxide detector having a borosilicate substrate. It may also have a carbon dioxide responsive indicator solution disposed on the borosilicate substrate. The carbon dioxide detector may be part of a carbon dioxide detector system also including an air intake operably connected to the housing to allow air to reach the carbon dioxide detector. The carbon dioxide detector may include a borosilicate substrate and a carbon dioxide responsive indicator solution disposed on the borosilicate substrate. This detector may be part of a further system, such as a resuscitation system. The detector may be made by wetting a borosilicate substrate with a carbon dioxide responsive indicator solution and drying the indicator solution to immobilize it and form a dried carbon dioxide detector. It may be used to detect the concentration of carbon dioxide in an air sample by exposing the detector to the sample.

20 Claims, 6 Drawing Sheets

U.S. PATENT DOCUMENTS

| | | | |
|---|---|---|---|
| 3,420,635 A | 1/1969 | Davis |
| 3,467,601 A | 9/1969 | Brauer |
| 3,505,022 A | 4/1970 | Luckey |
| 3,507,623 A | 4/1970 | McConnaughey |
| 3,556,122 A | 1/1971 | Laerdal |
| 3,612,048 A | 10/1971 | Takaoka et al. |
| 3,615,233 A | 10/1971 | Doering et al. |
| 3,659,586 A | 5/1972 | Johns et al. |
| 3,694,164 A | 9/1972 | Guenther |
| 3,754,867 A | 8/1973 | Guenther |
| 3,830,630 A | 8/1974 | Kiefer et al. |
| 4,003,709 A | 1/1977 | Eaton et al. |
| 4,019,862 A | 4/1977 | Dahms |
| 4,077,404 A | 3/1978 | Elam |
| 4,106,502 A | 8/1978 | Wilson |
| 4,144,306 A | 3/1979 | Figueras |
| 4,277,251 A | 7/1981 | Leichnitz |
| 4,287,153 A | 9/1981 | Towsend |
| 4,332,771 A | 6/1982 | Leichnitz |
| 4,346,584 A | 8/1982 | Boehringer |
| 4,366,821 A | 1/1983 | Wittmaier et al. |
| 4,389,372 A | 6/1983 | Lalin |
| 4,438,067 A | 3/1984 | Siddiqi |
| 4,548,906 A | 10/1985 | Sekikawa et al. |
| 4,557,900 A | 12/1985 | Heitzmann |
| 4,557,901 A | 12/1985 | Koyama et al. |
| 4,691,701 A | 9/1987 | Williams |
| 4,728,499 A | 3/1988 | Fehder |
| 4,734,125 A | 3/1988 | Gehring et al. |
| 4,774,941 A | 10/1988 | Cook |
| 4,780,411 A | 10/1988 | Piejko et al. |
| 4,788,153 A | 11/1988 | Detwiler et al. |
| 4,790,327 A | 12/1988 | Despotis |
| 4,805,623 A | 2/1989 | Jobsis |
| 4,824,640 A | 4/1989 | Hildenbrand et al. |
| 4,879,999 A | 11/1989 | Leiman et al. |
| 4,890,619 A | 1/1990 | Hatschek |
| 4,928,687 A | 5/1990 | Lampotang et al. |
| 4,945,918 A | 8/1990 | Abernathy |
| 4,994,117 A | 2/1991 | Fehder |
| 4,999,306 A | 3/1991 | Yafuso et al. |
| 5,005,572 A * | 4/1991 | Raemer et al. ........... 128/207.14 |
| 5,109,840 A | 5/1992 | Daleiden |
| 5,124,129 A | 6/1992 | Riccitelli et al. |
| 5,156,159 A | 10/1992 | Lampotang et al. |
| 5,166,075 A | 11/1992 | Fehder |
| 5,179,002 A | 1/1993 | Fehder |
| 5,197,464 A | 3/1993 | Babb et al. |
| 5,204,922 A | 4/1993 | Weir et al. |
| 5,250,095 A * | 10/1993 | Sigel et al. ........................ 65/378 |
| 5,279,289 A | 1/1994 | Kirk |
| 5,291,879 A | 3/1994 | Babb et al. |
| 5,322,612 A | 6/1994 | Abe et al. |
| 5,361,758 A | 11/1994 | Hall et al. |
| 5,375,592 A | 12/1994 | Kirk et al. |
| 5,456,249 A | 10/1995 | Kirk |
| 5,468,451 A | 11/1995 | Gedeon |
| 5,472,668 A | 12/1995 | Mills et al. |
| 5,480,611 A | 1/1996 | Mills et al. |
| 5,494,032 A | 2/1996 | Robinson et al. |
| 5,494,640 A | 2/1996 | Simon et al. |
| 5,517,985 A | 5/1996 | Kirk et al. |
| 5,520,997 A | 5/1996 | Pourahmady et al. |
| 5,634,426 A | 6/1997 | Tomlinson et al. |
| 5,679,884 A | 10/1997 | Kirk |
| 5,714,121 A | 2/1998 | Alderete et al. |
| 5,749,358 A | 5/1998 | Good et al. |
| 5,783,110 A | 7/1998 | Verdicchio et al. |
| 5,846,836 A | 12/1998 | Mallow |
| 5,849,594 A | 12/1998 | Balderson et al. |
| 6,055,447 A | 4/2000 | Weil et al. |
| 6,058,933 A | 5/2000 | Good et al. |
| 6,123,075 A | 9/2000 | Kirk |
| 6,216,024 B1 | 4/2001 | Weil et al. |
| 6,265,221 B1 | 7/2001 | Nilsson |
| 6,319,723 B1 | 11/2001 | Jeffers et al. |
| 6,378,522 B1 | 4/2002 | Pagan |
| 6,427,687 B1 | 8/2002 | Kirk |
| 6,428,748 B1 | 8/2002 | Wallach |
| 6,436,347 B1 | 8/2002 | Cedeon |
| 6,502,573 B1 | 1/2003 | Ratner |
| 6,576,474 B2 | 6/2003 | Wallach |
| D478,522 S | 8/2003 | Geist |
| 6,654,622 B1 | 11/2003 | Eberhard et al. |
| 6,670,115 B1 | 12/2003 | Zhang |
| 6,677,159 B1 | 1/2004 | Mallow |
| 6,709,403 B1 | 3/2004 | Ratner |
| 6,731,963 B2 | 5/2004 | Finarov et al. |
| 6,802,812 B1 | 10/2004 | Walker et al. |
| 6,816,266 B2 | 11/2004 | Varshneya et al. |
| 6,929,008 B2 | 8/2005 | Geist |
| 6,934,571 B2 | 8/2005 | Wiesmann et al. |
| 7,017,578 B2 | 3/2006 | Tresnak et al. |
| 7,024,235 B2 | 4/2006 | Melker et al. |
| 7,127,278 B2 | 10/2006 | Melker et al. |
| 7,140,370 B2 | 11/2006 | Tresnak et al. |
| 7,319,894 B2 | 1/2008 | Higgins |
| 7,341,560 B2 | 3/2008 | Henderson et al. |
| 7,392,074 B2 | 6/2008 | Isaacson et al. |
| 7,440,788 B2 | 10/2008 | Jenkins et al. |
| 2002/0128544 A1 | 9/2002 | Diab et al. |
| 2003/0003593 A1 | 1/2003 | Wallach |
| 2003/0133123 A1 | 7/2003 | Yeh |
| 2003/0199095 A1 | 10/2003 | Yuyama et al. |
| 2004/0065329 A1 | 4/2004 | Geist |
| 2004/0184024 A1 | 9/2004 | Katura et al. |
| 2004/0230108 A1 | 11/2004 | Melker et al. |
| 2004/0260161 A1 | 12/2004 | Melker et al. |
| 2005/0016543 A1 | 1/2005 | Geist |
| 2005/0039751 A1 | 2/2005 | Pagan |
| 2005/0049468 A1 | 3/2005 | Carlson et al. |
| 2005/0059869 A1 | 3/2005 | Scharf et al. |
| 2005/0113704 A1 | 5/2005 | Lawson et al. |
| 2006/0020179 A1 | 1/2006 | Anderson et al. |
| 2006/0167351 A1 | 7/2006 | Isaacson et al. |
| 2007/0060809 A1 | 3/2007 | Higgins |
| 2007/0078318 A1 | 4/2007 | Kling et al. |
| 2008/0076980 A1 | 3/2008 | Hoarau |
| 2008/0076981 A1 | 3/2008 | Hoarau |
| 2008/0076994 A1 | 3/2008 | Hoarau |
| 2008/0076995 A1 | 3/2008 | Hoarau |
| 2008/0076996 A1 | 3/2008 | Hoarau |
| 2008/0108887 A1 | 5/2008 | Higgins |
| 2008/0139908 A1 | 6/2008 | Kurth |
| 2008/0262328 A1 | 10/2008 | Adams |

FOREIGN PATENT DOCUMENTS

| | | |
|---|---|---|
| EP | 0 481 719 A1 | 4/1992 |
| EP | 0 307 625 B1 | 4/1994 |
| EP | 0 257 916 A1 | 1/1995 |
| EP | 0 509 998 B1 | 1/1996 |
| EP | 0 451 719 B1 | 12/1996 |
| EP | 0 601 171 B1 | 9/1997 |
| EP | 0 592 632 B1 | 8/1999 |
| EP | 01 022 558 A2 | 7/2000 |
| EP | 1 022 558 A3 | 7/2000 |
| EP | 1 039 294 A2 | 9/2000 |
| EP | 1 039 294 A3 | 10/2000 |
| EP | 630203 | 7/2002 |
| EP | 1 245 947 A1 | 10/2002 |
| EP | 1 266 944 A1 | 12/2002 |
| EP | 0 858 594 B1 | 4/2003 |
| EP | 1 327 874 A2 | 7/2003 |
| EP | 1 153 294 B1 | 10/2003 |
| EP | 0 943 093 B1 | 11/2003 |
| EP | 1491135 | 12/2004 |
| EP | 1986543 | 11/2008 |
| GB | 1 043 988 A | 9/1966 |
| GB | 2405100 | 2/2005 |
| JP | 07072081 | 3/1995 |
| JP | 08145979 A | 6/1996 |
| JP | 08247997 A | 9/1996 |
| JP | 09318528 A | 12/1997 |
| JP | 10073560 A | 3/1998 |
| JP | 2003072857 A | 3/2003 |

| | | | |
|---|---|---|---|
| JP | 2004177247 A | 6/2004 | |
| JP | 2005054048 A | 3/2005 | |
| WO | WO 90/01695 A1 | 2/1990 | |
| WO | WO 90/03819 A1 | 4/1990 | |
| WO | WO 91/05252 A1 | 4/1991 | |
| WO | WO 92/20404 A1 | 11/1992 | |
| WO | WO9316629 | 9/1993 | |
| WO | WO 93/20431 A1 | 10/1993 | |
| WO | WO 94/00756 A1 | 1/1994 | |
| WO | WO 96/19727 A1 | 6/1996 | |
| WO | WO 96/24054 A1 | 8/1996 | |
| WO | WO 97/10496 A1 | 3/1997 | |
| WO | WO 97/12227 A1 | 4/1997 | |
| WO | WO9817174 | 4/1998 | |
| WO | WO 98/26283 A1 | 6/1998 | |
| WO | WO 00/29830 A1 | 5/2000 | |
| WO | WO 00/43778 A1 | 7/2000 | |
| WO | WO 01/04624 A1 | 1/2001 | |
| WO | WO 0106248 | 1/2001 | |
| WO | WO 01/44385 A1 | 6/2001 | |
| WO | WO 03/045608 A1 | 3/2003 | |
| WO | WO 2004/077035 A1 | 9/2004 | |
| WO | WO2006124696 | 11/2006 | |
| WO | WO2007013054 | 2/2007 | |
| WO | WO2007041331 | 4/2007 | |
| WO | WO2007086856 | 8/2007 | |
| WO | WO2008019294 | 2/2008 | |
| WO | WO2008020845 | 2/2008 | |
| WO | WO2008039391 | 4/2008 | |

OTHER PUBLICATIONS

S.G.R.G. Barton et al.; "Expression of heat shock protein 32 (hemoxygenase-1) in the normal and inflamed human stomach and colon: an immunohistochemical study"; Cell Stress & Chaperones, vol. 8, No. 4; pp. 329-334 (2003).

Jessy Deshane et al.; "Heme oxygenase-1 expression in disease states"; Acta Biochimica Polonica, vol. 52, No. 2; pp. 273-284 (2005).

Shai Efrati, MD et al.; "Optimization of Endotracheal Tube Cuff Filling by Continuous Upper Airway Carbon Dioxide Monitoring"; Anesth. Analg; vol. 101, pp. 1081-1088 (2005).

Shai Efrati, MD; "Is Capnometry the Optimum Method for Assessing the Adequacy of Endotracheal Tube Cuff Seal?"; Anesthesia & Analgesia; vol. 103, No. 2; pp. 505-506 (Aug. 2006).

Shaw-Fang Yet et al.; "Heme Oxygenase 1 in Regulation of Inflammation and Oxidative Damage"; Methods in Enzymology; vol. 353, pp. 163-176 (2002).

M.R. Shahriari, Q. Zhou, and G.H. Sigel, Jr., Porous optical fibers for high-sensitivity ammonia-vapor sensors, 1988,Optical Society of America, May 1988, vol. 13, No. 5, pp. 407-409.

J.A. Berman et al.; "The Einstein Carbon Dioxide Detector"; Anesthesiology, vol. 60, No. 6; pp. 613-614 (1984).

P.K. Birmingham et al.; "Esophageal Intubation: A Review of Detection Techniques"; Anesth. Analg.; vol. 65; pp. 886-891 (1986).

* cited by examiner

CARBON DIOXIDE DETECTOR HAVING BOROSILICATE SUBSTRATE

TECHNICAL FIELD

The present disclosure relates to a carbon dioxide detector having a borosilicate substrate.

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Respiratory gasses may be readily distinguished from non-respiratory gasses by carbon dioxide content. Exhaled respiratory gas in a human typically contains between 3% and 5% carbon dioxide. In contrast, ambient air has only approximately 0.03% carbon dioxide. Normal esophageal gas has similarly low levels of carbon dioxide.

The detection of respiratory gasses via carbon dioxide content may be useful in a variety of circumstances. For example, one may determine whether an endotracheal tube has been correctly placed in the trachea rather than in the esophagus by detecting the presence of carbon dioxide in air exiting the tube. If carbon dioxide levels consistent with respiration are present, then the tube is correctly placed. If only low carbon dioxide levels consistent with placement in the esophagus are present, then the tube may have been incorrectly placed and may need to be removed and reinserted correctly. Additionally, if a tracheal tube is present in the trachea, but carbon dioxide levels in respired gas are low, this may be indicative of perfusion failure.

Continued detection of carbon dioxide in respired gas may also be useful in determining if an endotracheal tube has been dislodged and if breathing and perfusion continue to be normal.

Current products can detect carbon dioxide in respired air using various chemicals sensitive to the presence of carbon dioxide on a substrate such as cellulose filter paper, for example Whatman paper.

SUMMARY

Certain aspects commensurate in scope with the disclosed embodiments are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

The present disclosure relates to a carbon dioxide detector having a borosilicate substrate.

In one embodiment it relates to a carbon dioxide detector having a borosilicate substrate and a carbon dioxide responsive indicator solution disposed on the borosilicate substrate.

In another embodiment it relates to a carbon dioxide detector system having a carbon dioxide detector, a housing containing the carbon dioxide detector, and an air intake operably connected to the housing to allow air to reach the carbon dioxide detector. The carbon dioxide detector may include a borosilicate substrate and a carbon dioxide responsive indicator solution disposed on the borosilicate substrate.

In another embodiment it relates to a carbon dioxide detector system having a means for detecting carbon dioxide. The means may include a borosilicate substrate. It may also include a housing means to contain the means for detecting carbon dioxide and an air intake means operably to allow air to reach the means for detecting carbon dioxide.

In another embodiment it relates to a resuscitation system having a carbon dioxide detector system, a resuscitator housing fitted with the carbon dioxide detector system, and a bag attached to the resuscitator housing. The carbon dioxide detector system may have a carbon dioxide detector, a housing containing the carbon dioxide detector, and an air intake operably connected to the housing to allow air to reach the carbon dioxide detector. The carbon dioxide detector may include a borosilicate substrate and a carbon dioxide responsive indicator solution disposed on the borosilicate substrate.

Another embodiment relates to a method of manufacturing a carbon dioxide detector. The method may include wetting a borosilicate substrate with a carbon dioxide responsive indicator solution and drying the indicator solution to immobilize it on the substrate and form a dried carbon dioxide detector.

Another embodiment relates to a method of detecting carbon dioxide concentration in an air sample. The method may include exposing a carbon dioxide detector to the air sample. The carbon dioxide detector may include a borosilicate substrate and a carbon dioxide responsive indicator solution disposed on the borosilicate substrate. The method may also include determining the color of the indicator solution, wherein the color of the indicator solution indicates the carbon dioxide concentration in the air sample.

Still another embodiment relates to a carbon dioxide detector having a carbon dioxide responsive indicator solution disposed on a borosilicate substrate. The detector may retain acceptable carbon dioxide sensitivity for at least 7 days at a temperature of approximately 60° C.

Another example method relates to detecting carbon dioxide in a breath-to-breath manner. To perform this method, one may attach to a subject a carbon dioxide detector having a carbon dioxide responsive indicator solution disposed on a borosilicate substrate. One may measure the carbon dioxide in respired air at an interval corresponding to every breath of the subject.

Yet another example method of detecting carbon dioxide includes providing an air sample to a carbon dioxide detector having a carbon dioxide responsive indicator solution disposed on a borosilicate substrate. One may measure the carbon dioxide in the air sample in a time frame between approximately 1 to 20 seconds.

Another embodiment relates to a carbon dioxide detector having a carbon dioxide responsive indicator solution disposed on a borosilicate substrate. The detector may retain acceptable carbon dioxide sensitivity during at least two hours of exposure to humid air.

An example method for determining whether a gaseous sample contains a predetermined concentration of carbon dioxide includes contacting the gaseous sample with a carbon dioxide detector having a carbon dioxide sensitive indicator disposed on a borosilicate substrate to detect carbon dioxide in the gaseous sample.

Another embodiment relates to an endotracheal device. The device may include a tubular housing having one end adapted for insertion into a subject's trachea and an other end adapted for placement external of the subject, the housing defining a lumen therethrough from one end to the other end for allowing bidirectional passage of air into and out of the subject to ventilate the subject's lungs. It may also include a carbon dioxide detector having a carbon dioxide sensitive indicator disposed on a borosilicate substrate placed within the lumen for determining the presence of carbon dioxide therein while still permitting unimpeded bidirectional flow of air therethrough to ventilate the subject's lungs.

Yet another embodiment relates to carbon dioxide detector that includes a borosilicate substrate; and a carbon dioxide responsive indicator solution disposed on the borosilicate substrate, wherein the indicator solution changes from purple to tan in the presence of carbon dioxide above a first level.

Yet another embodiment relates to carbon dioxide detector that includes a borosilicate substrate; and a carbon dioxide responsive indicator solution disposed on the borosilicate substrate, wherein the indicator solution changes color in less than 1 second in the presence of carbon dioxide above a first level.

Finally, another embodiment relates to carbon dioxide detector that includes a borosilicate substrate; and a carbon dioxide responsive indicator solution disposed on the borosilicate substrate, wherein the indicator solution is adapted to change from color in the presence of carbon dioxide after a shelf life of greater than five years.

BRIEF DESCRIPTION OF THE DRAWINGS

A more complete understanding of the present disclosure thereof may be acquired by referring to the following description taken in conjunction with the accompanying drawings. These drawings represent only certain embodiments of the present disclosure.

While the present disclosure is susceptible to various modifications and alternative forms, specific example embodiments thereof have been shown in the drawings and are herein described in detail. It should be understood, however, that the description herein of specific example embodiments is not intended to limit the disclosure to the particular forms disclosed herein, but on the contrary, this disclosure is to cover all modifications and equivalents as defined by the appended claims.

DETAILED DESCRIPTION

The present disclosure relates to a colorimetric carbon dioxide detector having a borosilicate substrate.

Figure 1:
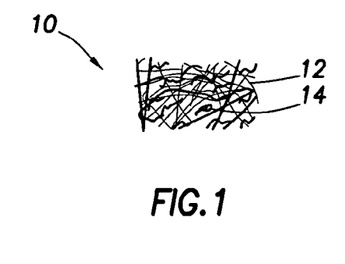
FIG. 1 illustrates a colorimetric carbon dioxide detector according to an exemplary embodiment of the present disclosure.

In a specific embodiment, shown in FIG. 1, detector 10 may include substrate 12 and indicator solution 14. Detector 10 may be sized appropriately for use in a detector system, such as those shown in FIGS. 2 and 3.

Substrate 12 may include any borosilicate-containing material. Specifically, it may include borosilicate fibers. These fibers may be produced using any conventional methods, such as melt blowing and spinning. The substrate may include a mesh of borosilicate fibers. More specifically, it may include a thin, highly porous mesh to facilitate rapid infiltration of carbon dioxide gas into the substrate.

Borosilicate may be sufficiently hydrophilic to allow indicator solution 14 to spread evenly over substrate 12 and be well absorbed when it is first applied. Indicator solution 14 may then be dried, but still retain sufficient water to allow reaction with carbon dioxide. However, the borosilicate substrate may also not be so hydrophobic that its shelf-life is compromised.

The borosilicate-containing material may also include an acrylic binder. In specific embodiments, this binder may be no more than 5% by weight or volume of the total substrate without indicator. Metrigard® membranes containing acrylic binder sold by Pall Corporation (New York) or a similar acrylic binder may be used.

Indicator solution 14 may contain an indicator, such as a chromogenic dye, in a solution. Indicator solution may be coated onto or impregnated into substrate 12. It may have a surface exposed to or near air or gas within carbon dioxide detector 10. Indicator solution 14 may be able to respond rapidly and positively to the presence or absence of certain concentrations of carbon dioxide. More specifically, it may be able to respond to concentrations of carbon dioxide normally present in air respired from a human, such as between approximately 2% and 5% or higher. Indicator solution 14 may also be able to respond to concentrations of carbon dioxide in air respired from a human with perfusion failure, such as concentrations between approximately 0.5% and 2%. Finally, indicator solution 14 may show no response to carbon dioxide concentrations normally present in external air or esophageal air, such as concentrations below approximately 0.5% and more specifically, concentrations between 0.03% and 0.5%.

Response times to changing carbon dioxide levels in detected air may be between approximately 1 and 20 seconds. Further, a borosilicate substrate 12 may exhibit virtually instantaneous response times of less than 1 second, which is an improvement over typical colorimetric carbon dioxide detection systems. Response may include a colorimetric indication, such as change of the indicator from one color to a very distinct second color. However, once the color begins to change, the change from one color to the other color may be virtually instantaneous as seen by the human eye.

In order to attain the above response properties, the indicator in indicator solution 14 may have a pK lower by 1.0-1.5 pH units than the pH of indicator solution 14. This difference allows indicator solution 14 to not change color instantly when exposed to air, allowing detector system 10 to be removed from packaging then connected to another device, such as a resuscitator. However, due to a greater resistance to negative effects of air exposure when a borosilicate or borosilicate+acrylic substrate is used as opposed to cellulose filter paper, an indicator pK outside of this range may still be acceptable. In general, any pK sufficient to allow carbon dioxide detector 10 to remain exposed to room or outside air for at least 15 minutes, at least 30 minutes, at least 60 minutes, or at least 120 minutes without significant color change may be sufficient.

Indicator solution 14 may include an alkaline solution containing hydroxyl ions or amine residues that react chemically with carbon dioxide to form a carbonate and/or a bicarbonate or carbamate moiety. This reaction may be represented by the following equations:

$$CO_2 + H_2O \leftrightarrow HCO_3^- + H^+ \qquad \text{I.}$$

$$CO_2 + H_2O \leftrightarrow CO_3^{2-} + 2H^+ \qquad \text{II.}$$

$$CO_2 + R_2NH \leftrightarrow R_2NCOO^- + H^+ \qquad \text{III.}$$

This reaction depletes the hydroxyl ion or amine at the interface between indicator solution 14 and air and this lowers the pH at the surface of indicator solution 14 where it is adjacent or nearly adjacent to air. This depletion results in the diffusion of new base from elsewhere in indicator solution 14 to its surface to maintain a surface pH similar to that of indicator solution 14 overall.

More specifically, the concentration of $OH^-$ or amine in the bulk of indicator solution 14 impregnated in or coated on substrate 12 helps determine the rate of diffusion of base to the surface of indicator solution 14. The rate of the chemical reaction at this surface is determined by the nature of each specific reacting species. The rate of reaction at the surface of indicator solution 14 may be expressed by the equation $R=K_A [CO_2][A]$, where [x] represents the concentration of a species in moles/liter and $K_A$ is a constant specific for reactant species A. In a specific embodiment, A is the indicator.

The balance of base between the surface and remainder of indicator solution 14 is also influenced by the contact time between the surface and the gas to which it is exposed, the composition of substrate 12, which determines the diffusivity constant for A and thus the rate of diffusion of A to the surface, and the concentration of carbon dioxide in the gas, which determines the rate of diffusion of carbon dioxide into or near the surface of the indicator where it may react with the indicator.

The concentration of $OH^-$ or amine in indicator solution 14, the rate of the chemical reaction, the contact time between the indicator surface and the gas and the diffusivity constant for A may all be pre-determined by the manner in which carbon dioxide detector 10 is constructed and the manner in which it is used. This leaves the concentration of carbon dioxide in the gas the only variable parameter with significant effect, allowing for its measurement.

The concentration of $OH^-$ or amine in indicator solution 14 and the rate of the chemical reaction may be selected such that the pH near the surface of indicator solution 14 decreases sufficiently in the presence of a certain concentration of carbon dioxide to cause a color change in indicator solution 14. For example, the color change may occur if the concentration of carbon dioxide in the tested air is greater than approximately 2%. This color change may occur within 1 to 20 seconds of exposure of carbon dioxide detector 10 to the air. In a specific example, a concentration of $OH^-$ sufficient to produce a pH of 9.6±0.2 in indicator solution 14 is sufficient to provide this sensitivity.

Embodiments of the present disclosure may also be utilized in areas other than breath-related carbon dioxide detectors. For example, they may be used to monitor the air in gas storage rooms, as an indicator in food packaging, as an air freshness indicator on airplanes or other areas where air is recycled, such as spacecraft, or as a room air freshness indicator for any enclosed space where a high density of people may gather. Sensitivity of the indicator solution and thus the detector may be selected to meet the needs of these and other embodiments. For example, some embodiments may need to be sensitive to and perhaps change color at different carbon dioxide concentrations than are recommended for a breath-related detector.

As noted above, the indicator may have a pK sufficiently lower than the pH of indicator solution 14 so that a color change does not occur upon exposure to room or outside air for a certain time period. Exposure to air causes the pH at the surface of indicator solution 14 to gradually decrease, but if such decrease is sufficiently slow, the desired time period without color change limitation may still be met.

The indicator used may affect which base is used to provide an alkaline indicator solution 14. For example, if the pK of the indicator is too low it is possible that with certain bases the pH of the indicator will not drop low enough to cause a color change in the presence of an elevated carbon dioxide concentration. For example, when a sodium hydroxide base is used the carbonate reaction product is water soluble and also a base. This buffers a pH decrease and may prevent the pH from reaching a level able to trigger a color change in the indicating element if the indicator has a low pK.

Calcium hydroxide may be used as a base in embodiments of this description. Calcium hydroxide serves as a source of hydroxyl ions but its carbonate reaction product with carbon dioxide is insoluble and therefore unable to buffer indicator solution 14 against a decrease in pH. Thus calcium hydroxide may be used with indicators having relatively low pKs, such as metacresol purple rather than, for example, thymol blue or phenol phthalein. This also allows for increased resistance to color change when exposed to room or external air. However, the use of a borosilicate or borosilicate+acrylic substrate 12 may allow use of a buffering source of hydroxyl ions in indicator solution 14.

Various colorless compounds may be used to provide an alkaline indicator solution 14. These include, but are not limited to calcium hydroxide, sodium carbonate, lithium hydroxide, sodium hydroxide, potassium hydroxide, magnesium hydroxide, potassium carbonate, sodium barbitol, tribasic sodium phosphate, dibasic sodium phosphate, potassium acetate, monoethanolamine, diethanolamine, and piperidine. However, if an acrylic-bound borosilicate is used as a substrate, no base may be needed.

Various pH sensitive indicators may also be used in indicator solution 14. These include, but are not limited to metacresol purple, thymol blue, cresol red, phenol red, xylenol blue, a 3:1 mixture of cresol red and thymol blue, bromothymol blue, neutral red, phenolphthalein, rosolic acid, α-naphthelphthalein, and orange I. Other pH indicators, the color change that occurs, and the relevant pH as well as other information may be found in the CRC Handbook of Chemistry and Physics, 8-17, 75th Edition 1994.

Indicator solution 14 may also contain a hygroscopic, high-boiling, transparent, colorless, water-miscible liquid. This liquid may entrap sufficient water in indicator solution 14 when it is coated onto or impregnated into substrate 12 to allow reaction of the surface of indicator 14 with carbon dioxide present in carbon dioxide detector 10.

Example hygroscopic, high-boiling, transparent, colorless, water-miscible liquids that may be used in indicator solution 14 include, but are not limited to glycerol, propylene glycol, monoethylene glycol, diethylene glycol, polyethylene glycol, and aliphatic alcohols. In specific embodiments, glycerol and propylene glycol or mixtures thereof may be used because of their antiseptic and non-toxic properties. Acrylic binder used in some embodiments of the disclosure also increases the hydrophobicity of substrate 12 and may thus decrease the need for a hygroscopic, high-boiling, transparent, colorless, water-miscible liquid in indicator solution 14.

Indicator solution 14 may be in an aqueous solution, or it may not be in solution in water. It may require or benefit from the presence of water, or may function independently of water. Indicator solution 14 may also be any type of chromogenic agent. For example, it may be a chromogenic agent that does not go into solution in water, but that nevertheless relies on nearby water.

When used, an acrylic binder provides a more basic environment for an indicator and also increases the hydrophobicity of the substrate. A basic environment may help keep the color of the indicator appropriate in a low $CO_2$, such as less than 0.5%, environment. Acrylic is an electron rich compound, which makes it a good Bronstead and Lewis base. The resulting ability to accept protons from proton rich compounds and to donate a pair of electrons to electron poor compounds allows the indicator to remain unreacted. Enough carbonic acid is formed to affect the indicator, but some of the acid is reacted by the acrylic.

A desired ratio of proton acceptance to compound concentration may be determined for different detectors. Varying the concentration of the acrylic binder will have an effect on the amount of carbonic acid available to react with the indicator when carbon dioxide is present in larger amounts. Thus, carbon dioxide detectors 10 that also contain acrylic binder in substrate 12 may not need sodium carbonate because the binder itself may provide a more basic environment for the indicator. When acrylic binder is used, the final color of dried indicator may also be less sensitive to changes in the pH of indicator solution 14. This may allow for a decrease in the amount of indicator in indicator solution 14 by as much as approximately 66% as compared to cellulose-based carbon dioxide detectors.

In a specific embodiment, used herein with all Metrigard® membrane tests, indicator solution 14 may include 0.0169 g of cresol red, 275 mL triethylene glycol, and 725 mL deionized water. This indicator solution may lack carbonate.

Indicator solution 14 may be immobilized on substrate 12 by drying, which removes a substantial amount of water. However, the reaction between the indicator and carbon dioxide may require water. Therefore, some water may be absorbed by indicator solution 14 and/or substrate 12 before use. For example, water may be absorbed from ambient air. In a specific embodiment, sufficient water may be absorbed in the time period required to remove carbon dioxide detector 10 from protective packaging and begin its actual use. For example, sufficient water may be absorbed by indicator solution 14 in less than 10, 5 or 1 seconds after the opening of any protective packaging.

Indicator solution 14 may also be placed on substrate 12 in various other forms or using other methods. For example, it may be provided in a hydrogel. Substrate 12 may also be treated, for example by plasma treatment, prior to administration of indicator solution 14.

Use of a borosilicate substrate may result in desirable response time and shelf life of a carbon dioxide detector, while retaining the capacity of the detector to cycle from one color to another quickly from breath to breath. For example, in some carbon dioxide detectors, reaction of the substrate with cresol red, which is used as a color indicator, eventually changes the color indicator irreversibly from purple to yellow. This change makes the detector color insensitive to the presence or absence of carbon dioxide. As a result, the detector system is no longer functional. Although packaging can help prevent this sensor aging, it nevertheless may limit shelf life. Borosilicate substrates do not react with cresol red. As a result, the same shelf life as is obtained with other substrates may be achieved with borosilicate and more cost effective packaging, or, a longer shelf life even in the same packaging may be achieved. In certain embodiments, the shelf life of a borosilicate-based carbon dioxide detector may be greater than 5 years, great than 10 years, or greater than 14 years. Further, while the shelf life of a borosilicate-based carbon dioxide detector may be greatly improved, the packaging employed may be reduced, due to the stability of the borosilicate-based carbon dioxide detector. While other colorimetric carbon dioxide detection systems may employ desiccants to extend their shelf lives, a borosilicate-based carbon dioxide detector may achieve a long shelf life (e.g. several years) without the use of a dessicant.

Additionally, the borosilicate substrate 12 may exhibit an improved color cycling pattern in the presence of carbon dioxide. For example, with use of a common indicator solution 14, such as metacresol purple, the substrate 12 may change from a deep purple to a light tan color, rather than purple to yellow, in the presence of carbon dioxide. One advantage of a purple-to-tan color change rather than a purple-to-yellow color change is that the contrast ratio between purple and tan is particularly advantageous, allowing a healthcare worker to distinguish finer gradations of carbon dioxide levels. Further, the purple-to-tan color change is also helpful for people with color blindness, which most often impairs acuity in the green-yellow-red portion of the spectrum.

Figure 5A:
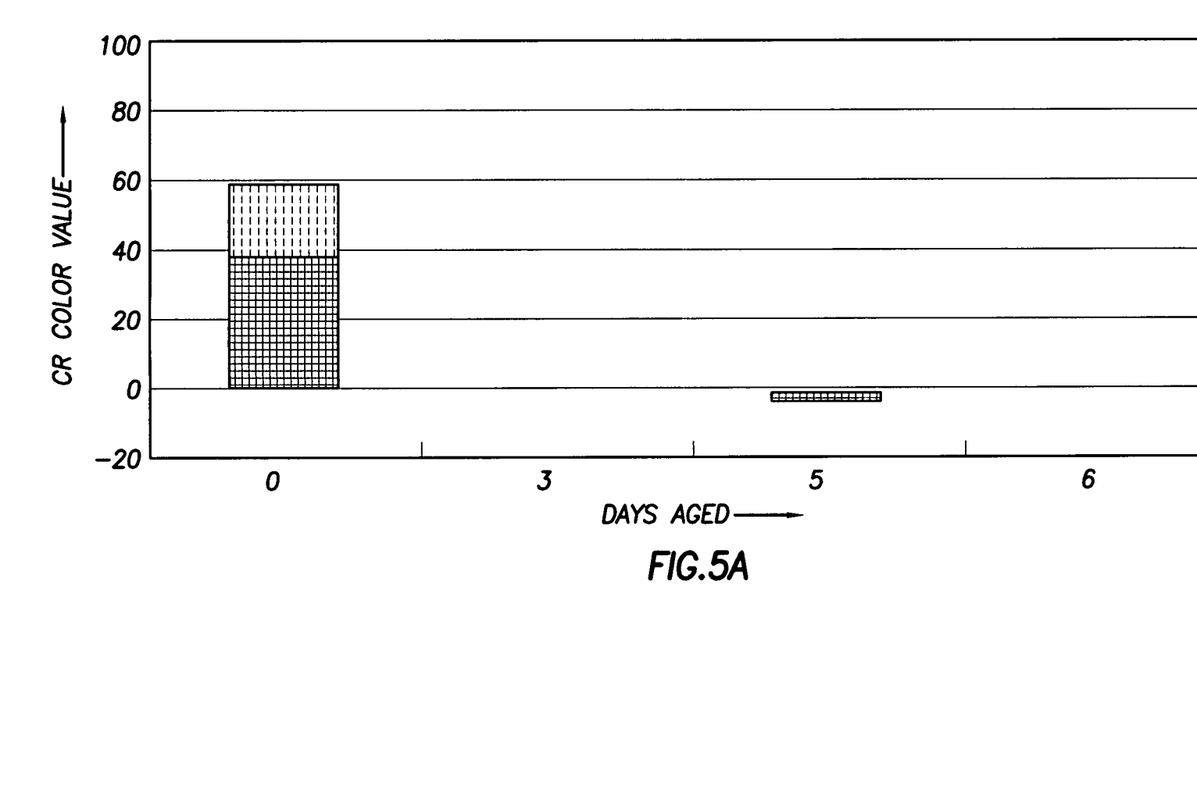
FIG. 5A shows the color transition of a previous cellulose carbon dioxide detector when exposed to room air and temperature. Light hash marks indicate yellow. Darker cross marks indicate purple.
Figure 5B:
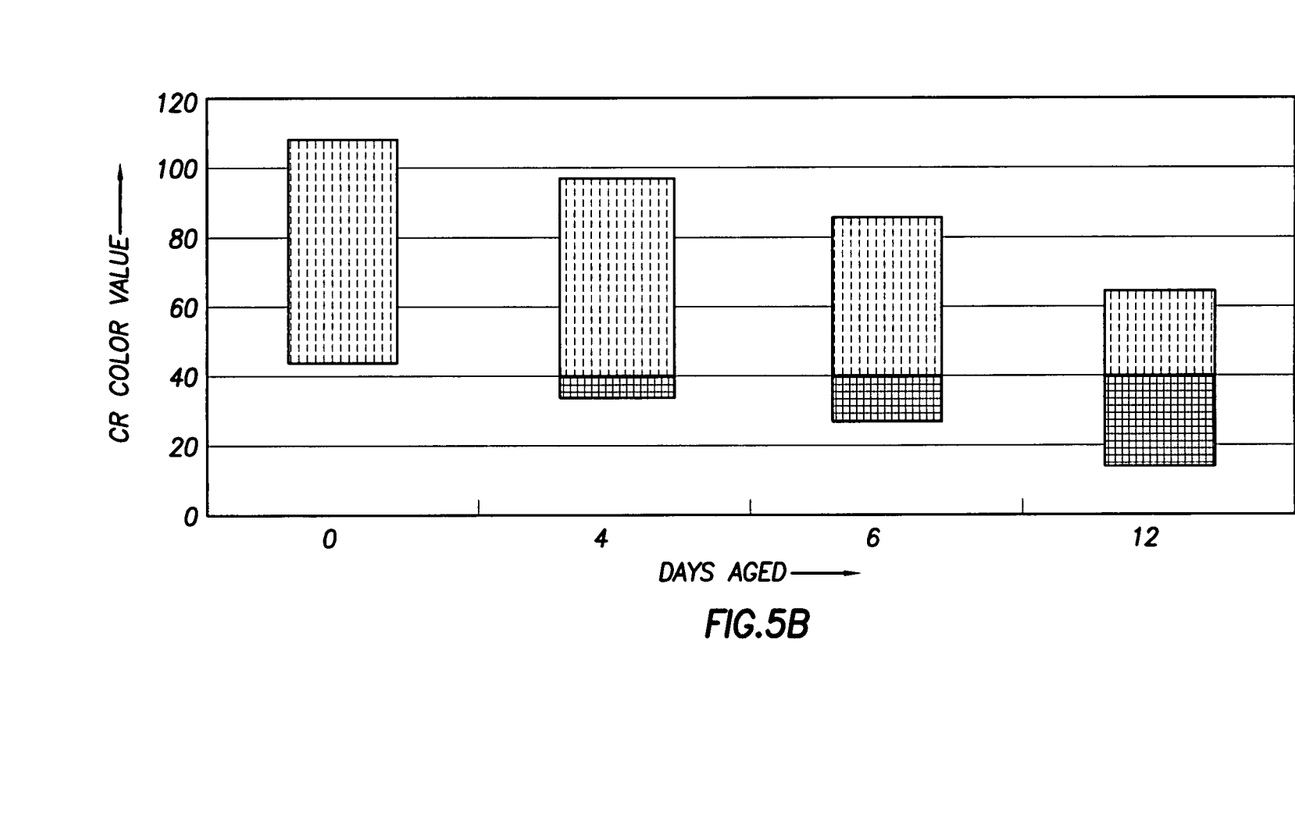
FIG. 5B shows the color transition of a carbon dioxide detector according to an embodiment of the present disclosure when exposed to room air and temperature. Light hash marks indicate yellow. Darker cross marks indicate purple.

Aging of borosilicate and cellulose detector systems was evaluated under exposure to room air. A detector system having cellulose as a substrate was exposed to room temperature. Color transition from purple to yellow results are shown in FIG. 5A. A detector system having borosilicate and acrylic as a substrate was also exposed to room temperature. Color transition from purple to yellow results are shown in FIG. 5B.

Indicator Color (CR Scale) in all Tables and Figures where used was determined using a Hunterlab LS6000 colorimeter and gas concentrations of 0.03, 1 and 2% $CO_2$ (balance $N_2$). The CR Scale is computed from the standard CIELab color scale as follows: CR=1.371*(a−b)+41.1. The CR color scale was devised so that a value of 0 corresponds to a bright yellow color while a value of 100 corresponds to deep purple. For the data shown in FIGS. 5 and 6, the highest value of the bar is the CR value measured when the indicator strip was exposed to 0.03% $CO_2$ (e.g. "room air"). The lowest value of the bar is the CR value measured when the indicator strip was exposed to 2% $CO_2$. The total length of the bar is therefore indicative of the extent of color change that is seen when the $CO_2$ concentration is transitioned between 0.03% and 2.0%. The shading of the bar was chosen using a CR value of 40 as the visual transition point between yellow and purple.

After only one day of exposure to air at room temperature, a significant transition from purple to yellow had taken place when a cellulose substrate was used. In contrast, using a similar carbon dioxide detector with a borosilicate and acrylic substrate (FIG. 5B), even after 12 days of exposure to air at room temperature, the sensitivity of the color indicator to $CO_2$ was greater than after only one day of exposure for the cellulose-based detector. Results of the experiments shown in FIG. 5 are presented in Table 1.

TABLE 1

Colorimetry of Carbon Dioxide Detectors after Aging at Room Temperature

| | | Indicator Color (CR Scale) | | |
|---|---|---|---|---|
| | | <0.03% $CO_2$ | <1% $CO_2$ | <2% $CO_2$ |
| Cellulose | Day 0 | 59.2 | 7.6 | −0.8 |
| | Day 3 | −2.2 | −2.4 | −2.5 |
| | Day 5 | −3.7 | −3.3 | −3.0 |
| | Day 6 | −1.7 | −1.2 | −0.8 |
| Borosilicate + acrylic | Day 0 | 108 | 57.2 | 43.2 |
| | Day 4 | 96.2 | 46.3 | 33.2 |
| | Day 6 | 84.9 | 37.5 | 26.7 |
| | Day 12 | 64.4 | 20.4 | 13.5 |

In Table 1, Metrigard® borosilicate membrane having acrylic binder (Pall Corporation, New York) was used in the borosilicate and acrylic detector.

Figure 6A:
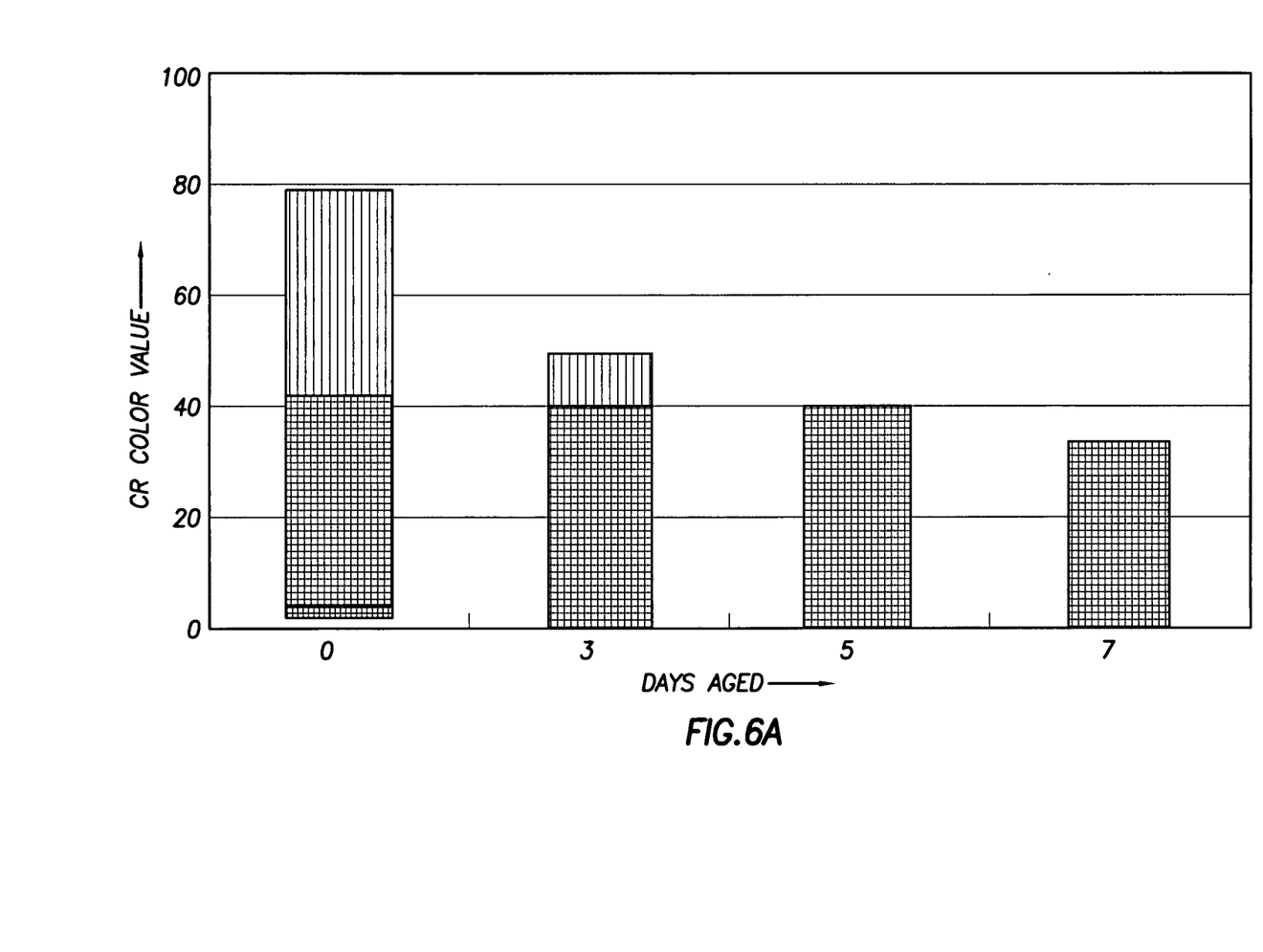
FIG. 6A shows the color transition of a previous carbon dioxide detector when aged at 60° C. in standard packaging. Light hash marks indicate yellow. Darker cross marks indicate purple.
Figure 6B:
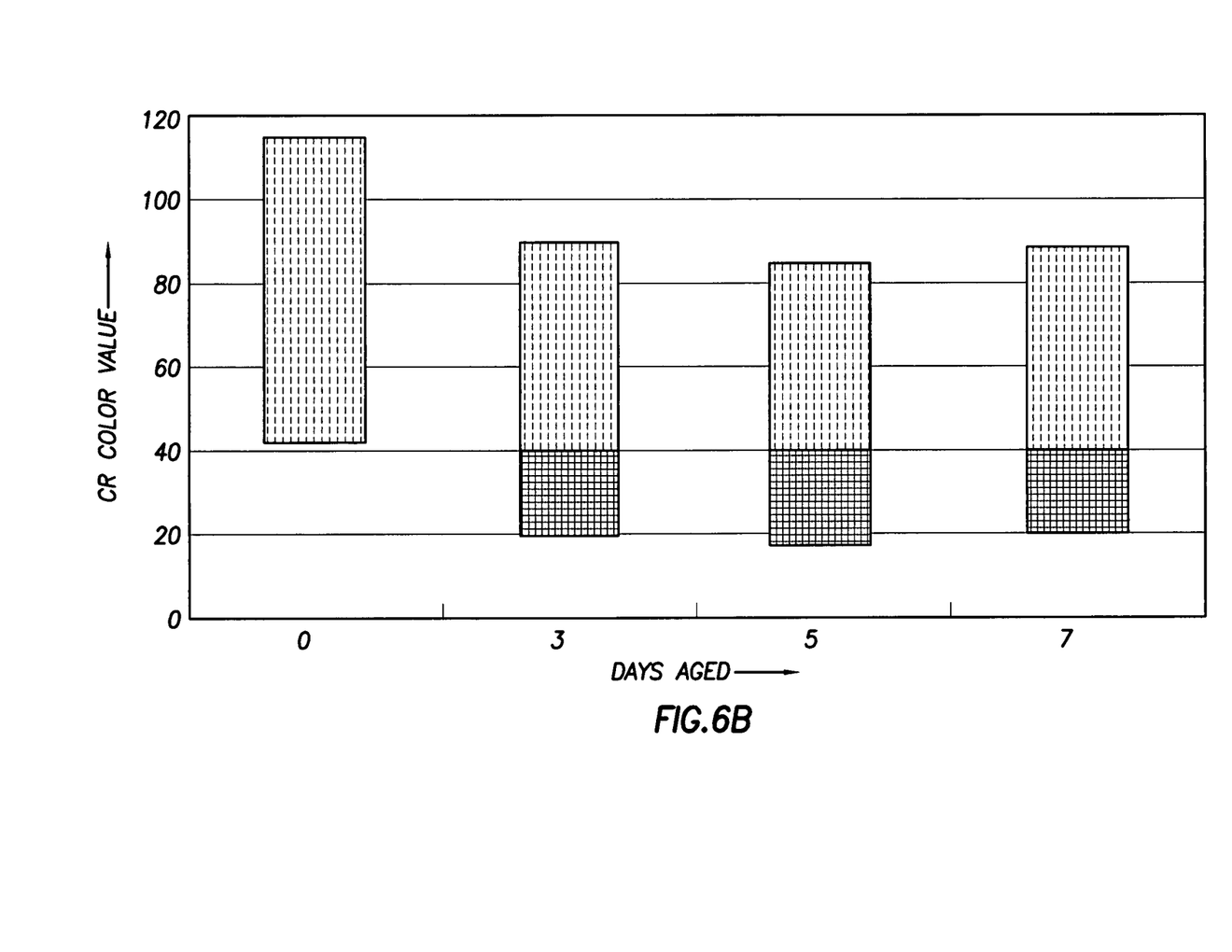
FIG. 6B shows the color transition of a carbon dioxide detector according to an embodiment of the present disclosure when aged at 60° C. in standard packaging. Light hash marks indicate yellow. Darker cross marks indicate purple.

FIG. 6A shows the rate of color change sensitivity to $CO_2$ in cellulose substrate detector systems under accelerated aging conditions. The data in FIG. 6A was collected by exposing a cellulose detector system in a sealed package in the presence of desiccant to 60° C. temperatures. The elevated temperature was used to allow the test to be performed more quickly. Elevated temperature increases the rate of cresol red reaction with substrate 12. As FIG. 6A shows, after 3 days of the accelerated ageing experiment, the cellulose-based carbon dioxide detectors have little sensitivity to the presence of carbon dioxide. FIG. 6B shows a similar test conducted with carbon dioxide detector system with a borosilicate and acrylic substrate. Even after 7 days of exposure to accelerated aging conditions, the sensitivity of the color indicator to $CO_2$ was quite high. Results of the experiments shown in FIG. 6 are presented in Table 2.

TABLE 2

Colorimetry of Carbon Dioxide Detectors after Accelerated Aging at 60° C.

| | | Indicator Color (CR Scale) | | |
|---|---|---|---|---|
| | | 0.03% | 1% | 2% |
| Cellulose | Day 0 | 77.3 | 13.4 | 1.5 |
| | Day 3 | 49.7 | 1.1 | −6.3 |
| | Day 5 | 39.8 | −1.4 | −7.5 |
| | Day 7 | 33.3 | −2.7 | −8.0 |
| Borosilicate + acrylic | Day 0 | 112.4 | 56.0 | 41.6 |
| | Day 3 | 88.6 | 29.4 | 18.9 |
| | Day 5 | 84.0 | 26.6 | 16.5 |
| | Day 7 | 87.8 | 30.8 | 20.3 |

In Table 2, Metrigard® borosilicate membrane having acrylic binder (Pall Corporation, New York) was used in the borosilicate and acrylic detector.

The performance of the borosilicate and acrylic binder-based detector described above was further evaluated sealed in a pouch in the absence of desiccant under accelerated aging conditions at even higher temperatures and for longer periods of time. Test conditions were otherwise as indicated above. These results are provided in Table 3.

The results of Table 3, as compared to those of Table 2, indicate that in some embodiments, a detector having a borosilicate substrate may be less sensitive to aging and have a longer shelf-life in the absence of desiccant rather than in its presence. Retention of acceptable carbon dioxide sensitivity during accelerated aging tests correlates with shelf-life.

TABLE 3

Colorimetry of Borosilicate Carbon Dioxide Detectors after Accelerated Aging

| | Aged 60° C. | | | Aged 70° C. | | | Aged 80° C. | | |
|---|---|---|---|---|---|---|---|---|---|
| [$CO_2$] | 0.03% | 1% | 2% | 0.03% | 1% | 2% | 0.03% | 1% | 2% |
| Day 0 | 107 | 46.4 | 34.1 | 95.5 | 45.6 | 33.9 | 98.6 | 47.5 | 35.5 |
| Day 1 | | | | | | | 92.7 | 38.1 | 27.7 |
| Day 4 | | | | | | | 72.7 | 26.5 | 19.0 |
| Day 5 | | | | | | | 71.7 | 26.2 | 18.7 |
| Day 6 | 93.2 | 39.2 | 28.7 | | | | 70.3 | 27.1 | 19.7 |
| Day 7 | | | | | | | 67.7 | 26.9 | 19.9 |
| Day 9 | | | | | | | 69.1 | 30.0 | 23.0 |
| Day 11 | | | | | | | 58.4 | 24.5 | 18.7 |
| Day 13 | 88.4 | 34.5 | 24.7 | | | | 56.7 | 25.4 | 19.8 |
| Day 15 | | | | 69.6 | 25.5 | 18.3 | 50.6 | 22.8 | 17.8 |
| Day 19 | | | | | | | 41.4 | 21.2 | 17.3 |
| Day 20 | 84 | 30.8 | 21.9 | | | | | | |
| Day 22 | | | | | | | 46.8 | 24.0 | 19.5 |
| Day 25 | | | | | | | 37.9 | 20.6 | 17.0 |
| Day 27 | 82 | 30.7 | 22.2 | | | | | | |
| Day 29 | | | | 61.1 | 23.4 | 17.3 | 33.6 | 20.1 | 17.0 |
| Day 34 | 83.2 | 32.2 | 23.5 | | | | | | |
| Day 36 | | | | 59.1 | 23.7 | 17.8 | | | |
| Day 42 | 78.0 | 27.5 | 19.2 | | | | | | |
| Day 43 | | | | 50.3 | 20.7 | 15.8 | | | |
| Day 48 | 70.5 | 22.9 | 15.6 | | | | | | |
| Day 50 | | | | 52.7 | 22.5 | 17.4 | | | |
| Day 55 | 73.1 | 26.3 | 18.7 | 49.7 | 20.7 | 15.8 | | | |
| Day 62 | 70.3 | 25.0 | 17.8 | | | | | | |

Based on these test results, a borosilicate based detector may be provided in packaging without desiccant. This packaging may include gas-impermeable metallic foil. The device may also be sealed under an atmosphere substantially devoid of carbon dioxide. For example, the device may be sealed in packaging currently in use for carbon dioxide detector systems but without the need for desiccant.

Figure 7:
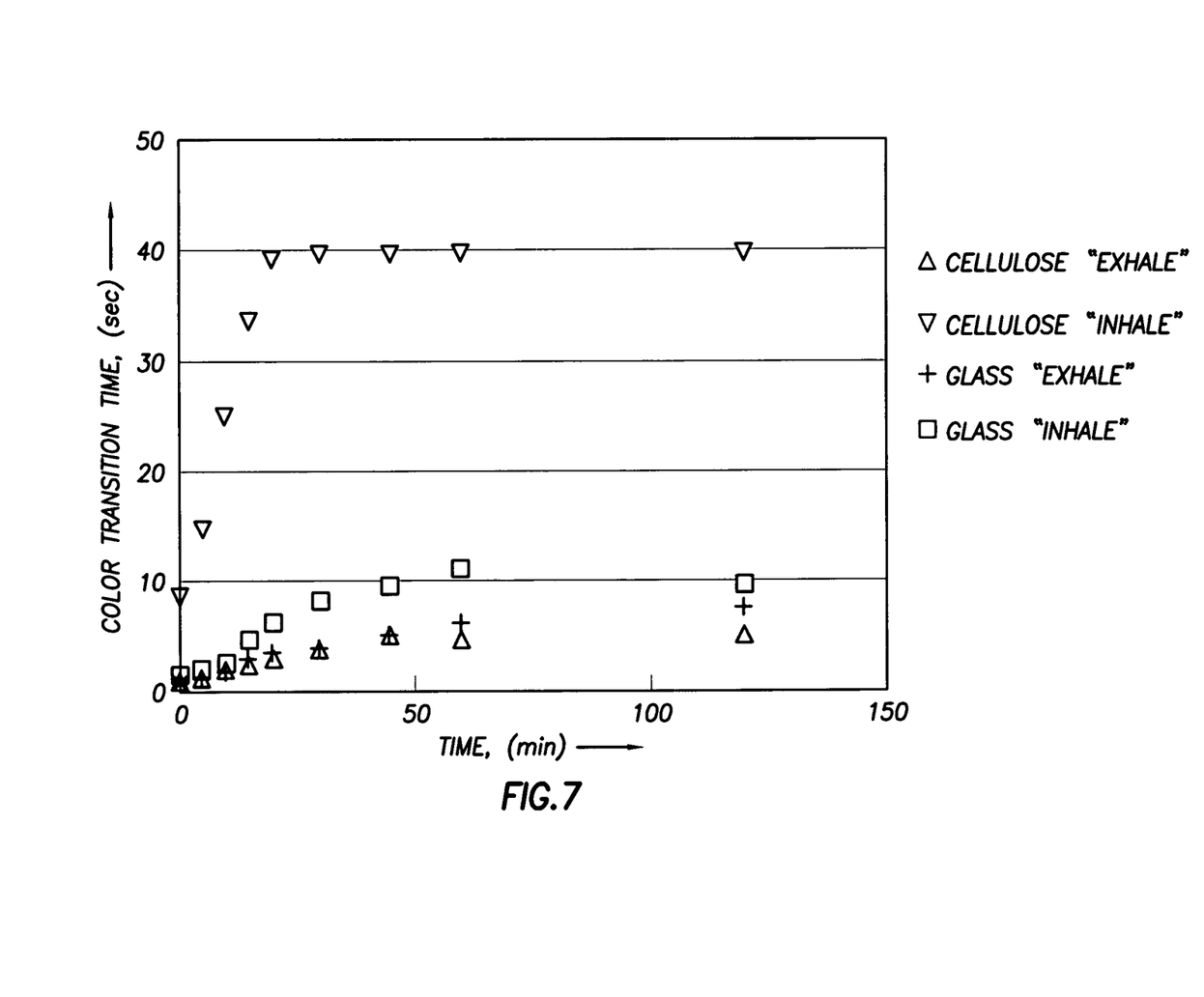
FIG. 7 shows the response time of two carbon dioxide detectors in humid air based on yellow to purple transition during inhalation and purple to yellow transition during exhalation.

Cellulose filter paper is strongly hydrophilic so that in warm, humid air, water is rapidly absorbed into the substrate. This reduces the responsivity of an indicator to changes in carbon dioxide concentration. The inhalation responsivity of a cellulose-based detector after exposure to humid air for certain time periods as compared to a detector of the present disclosure having a borosilicate and acrylic substrate is shown in FIG. 7. While both detectors show clinically useful responsiveness, The cellulose-based detector takes 13 seconds longer to respond to inhalation after 5 minutes of exposure to humid air. Data showing this difference is presented in FIG. 7. Response times of greater than 40 seconds were not timed for their full duration.

A cellulose-based detector as compared to a detector of the current invention with borosilicate and acrylic substrate displays similar sensitivity to exhalation after exposure to humid air. This is in contrast to results achieved during inhalation described above. These levels of responsiveness are expected because the chemical reaction necessary for color change during exhalation is less sensitive to humidity. These results are also presented in FIG. 7. Comparative data for both inhalation and exhalation is presented in Table 4.

TABLE 4

Response Time of Carbon Dioxide Detectors after Exposure to Humid Air

| Exposure Time (min) | Purple to Yellow (Exhalation) (sec) | | Yellow to Purple (Inhalation) (sec) | |
|---|---|---|---|---|
| | Cellulose | Borosilicate + Acrylic | Cellulose | Borosilicate + Acrylic |
| 0 | 1 | 1 | 9 | 2 |
| 5 | 1 | 1 | 15 | 2 |
| 10 | 2 | 2 | 26 | 3 |
| 15 | 3 | 3 | 34 | 5 |
| 20 | 3 | 4 | >40 | 6 |
| 30 | 4 | 4 | >40 | 8 |
| 45 | 5 | 5 | >40 | 10 |
| 60 | 5 | 6 | >40 | 11 |
| 120 | 5 | 8 | >40 | 10 |

In Table 4, Metrigard® borosilicate membrane having acrylic binder (Pall Corporation, New York) was used in the borosilicate and acrylic detector.

The performance of carbon dioxide detectors in humid air is significant to clinical use because exhaled breath contains considerable amounts of water. Thus, performance in humid conditions is indicative of performance with actual patients. It may affect the use-life of a detector. Accordingly, carbon dioxide detectors having a borosilicate and acrylic substrate show faster breath-to-breath response than those having a cellulose fiber substrate such as paper. This faster response is also facilitated by the highly porous nature of borosilicate, which allows easier penetration of air than does a cellulose fiber substrate. This may indicate a longer use-life of the borosilicate substrate detector.

Figure 2:
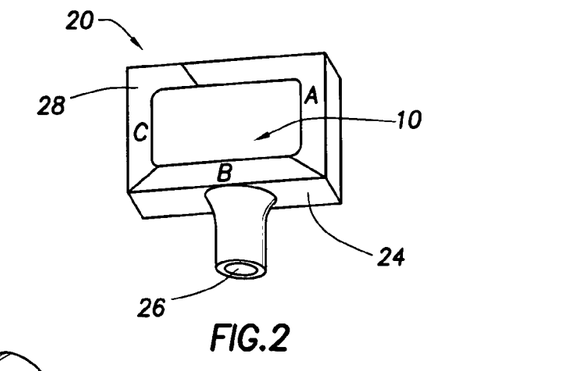
FIG. 2 illustrates another colorimetric carbon dioxide detector system according to an exemplary embodiment of the present disclosure.

In another specific embodiment, shown in FIG. 2, detector system 20 may include carbon dioxide detector 10, housing 24, air intake 26, and color indicators 28. Detector system 20 may be configured to fit into a further system, such as resuscitator 60. The further system may supply air to detector system 20 for measurement. Specifically, the further system may be connected to the respiratory pathway of a patient.

Parts of detector system 20, such as housing 24 and/or air intake 26 may be made from a rigid material. For example, they may be made from a plastic, such as a clear colorless, transparent plastic. By way of further example, housing 24 and/or air intake 26 may be made from polyethylene, polypropylene, an acrylic polymer such as PLEXIGLAS® polymer, polycarbonate, nylon, polysytrene, and styrene-acrylonitrile copolymer. At least a portion of housing 24 may be clear so as to allow viewing of carbon dioxide detector 10.

Air intake 26 may also serve to couple detector system 20 with any further system. It may be releasably secured to housing 24, such as by a threaded engagement, or it may form an integral unit with housing 24. Air intake 26 may also have a threaded engagement, tab or grooves, or other features to allow it to be releasably secured to any further system. For example, a pressure fit is used to couple the detector system to the manual resuscitator in the current INdGO/IndCAP™ products (Nellcor, Tyco Healthcare, California).

Color indicators 28 may approximately match the color of indicator solution 14 in the presence of difference levels of carbon dioxide. Color indicators 28 may also include written or other visual information to allow a user to determine what carbon dioxide concentrations are indicated by various colors. For example, region A may show one or various shades that correlate with a low carbon dioxide concentration, such as below approximately 0.5% or between approximately 0.03% and 0.5%. In a specific embodiment, region A may contain shades of purple. Region C may show one or various shades that correlate with a high carbon dioxide concentration typical of respired air, such as above approximately 2% or between 2% and 5%. In a specific embodiment, region C may contain shades of yellow. Optional region B may indicate carbon dioxide concentrations above that of normal or esophageal air, but below that corresponding with normal respiration. For example, region B may indicate carbon dioxide concentrations common in respired air of a patient suffering from perfusion failure. Region B may show one or various shades that correlate with carbon dioxide concentrations of between approximately 0.5% and 2%. In one specific embodiment, region B may contain shades of grayish purple.

Figure 3:
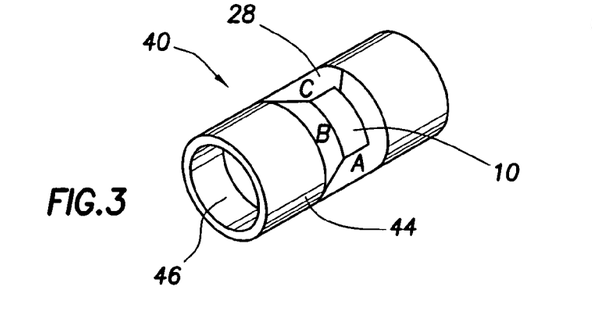
FIG. 3 illustrates a third colorimetric carbon dioxide detector system according to an exemplary embodiment of the present disclosure.

In yet another specific embodiment, shown in FIG. 3, detector system 40 may include carbon dioxide detector 10, housing 44, air intake 46, and color indicators 28. Housing 44 and air intake 46 may be similar to housing 24 and air intake 26 in composition and function. However, they may be of a different shape to allow use with other systems.

Figure 4:
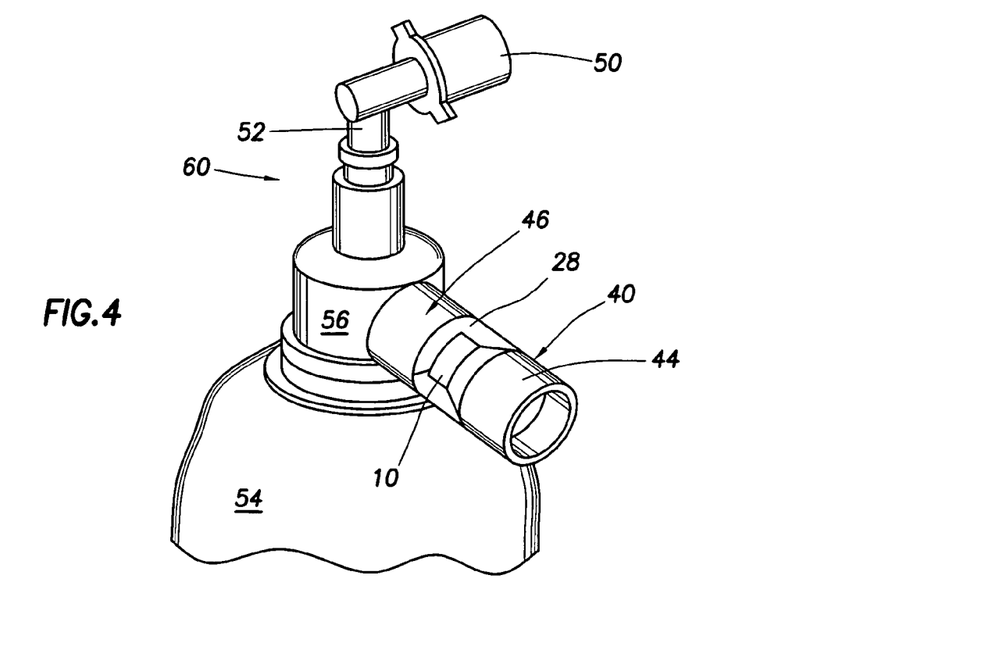
FIG. 4 illustrates a resuscitator having a colorimetric carbon dioxide detector system according to an exemplary embodiment of the present disclosure.

In another embodiment of the disclosure shown in FIG. 4 resuscitator 60 may include carbon dioxide detector system 40, which attaches to resuscitator housing 56. Carbon dioxide detector system 20 may also be used with resuscitator 60 (not shown). Resuscitator 60 may also have endotracheal tube attachment 50, swivel joint 52, and bag 54. Resuscitator 60 may be formed in any manner known to the art. In particular it may be formed in the manner of an INdGO™ disposable manual resuscitator (Nellcor, Tyco Healthcare, California).

Detection may include in-stream detection, such as in the current EasyCap™ (Nellcor, Tyco Healthcare, California) system. It may also include "side-stream" detection, such as in the current INdCAP™ product (Nellcor, Tyco Healthcare, California). The detection system may be modified to facilitate either form of detection.

Carbon dioxide detector 10 may be prepared by forming substrate 12 then impregnating or coating it with indicator solution 14. Substrate 12 may then be dried to immobilize indicator solution 14 on it. Substrate 12 may then be incorporated into a detector system such as those shown in FIGS. 2 and 3. The detector system may then be packaged in protective packaging. It may also be incorporated in a further system, such as resuscitator 60, before packaging. During its formation and handling prior to packaging, carbon dioxide detector 10 may be kept in conditions to minimize or control chemical reactions that might negatively influence its reliability. For example, it may be kept in dry conditions after drying. Carbon dioxide detectors of the present disclosure may require less stringent pre-packaging conditions than current cellulose filter paper detectors because of improvements in resistance to negative effects of humidity and room air. Carbon dioxide detectors, detection systems, of further systems such as resuscitators may be created in a sterile or clean environment or later sterilized.

Carbon dioxide detector 10 may be used by providing air to it. The air then infiltrates substrate 12 and any carbon dioxide in the air reacts with indicator solution 14. This may produce a color change in the indicator. Carbon dioxide detector 10 may specifically be used to detect air from an endotracheal tube. Such systems and method are discussed in the U.S. patent publication No. 20080077036, titled "CARBON DIOXIDE-SENSING AIRWAY PRODUCTS AND TECHNIQUE FOR USING THE SAME" to Clark R. Baker Jr., Roger Mecca, Michael P. O'Neil, and Rafael Ostrowski filed on Sep. 25, 2006, the specification of which is hereby incorporated by reference in its entirety. The presence of carbon dioxide may indicate proper placement of the tube in the trachea of a patient rather than in the esophagus. Carbon dioxide detector 10 may be able to detect such incorrect placement in sufficiently little time to allow removal of the tube and placement in the trachea before the patient suffers serious injury or death. Change color back and forth between a low carbon dioxide color to a high color dioxide color may indicate whether the patient is breathing normally. Change of color to one indicating low concentrations of carbon dioxide still above concentrations in air may indicate perfusion failure in the patient.

Carbon dioxide detector 10 may be used to monitor any patient benefiting from an endotracheal tube or other endotracheal system, e.g. a resuscitator fitted with a mask. More specifically, if may be used to monitor a human patient, such as a trauma victim, an anesthetized patient, a cardiac arrest victim, a patient suffering from airway obstruction, or a patient suffering from respiratory failure.

While embodiments of this disclosure have been depicted, described, and are defined by reference to specific example embodiments of the disclosure, such references do not imply a limitation on the disclosure, and no such limitation is to be inferred. The subject matter disclosed is capable of considerable modification, alteration, and equivalents in form and function, as will occur to those ordinarily skilled in the pertinent art and having the benefit of this disclosure. The depicted and described embodiments of this disclosure are examples only, and are not exhaustive of the scope of the disclosure. For example, the substrate may be formed in a variety of ways; various indicators, alkali sources and other components may be used in the indicator solution; the indicator solution may be placed on the substrate in a variety of ways; multiple indicators may be used to detect narrower ranges of carbon dioxide concentration; and the system may take a variety of shapes.

What is claimed is:

1. A method of detecting carbon dioxide concentration in an air sample comprising:
exposing a carbon dioxide detector to the air sample, wherein the carbon dioxide detector comprises:
a borosilicate substrate, having an acrylic binder; and;
a carbon dioxide responsive indicator solution disposed on the borosilicate substrate; and
determining the color of the indicator solution, wherein the color of the indicator solution indicates the carbon dioxide concentration in the air sample.

2. The method according to claim 1, wherein the air sample comprises air inhaled by a patient.

3. The method according to claim 1, wherein the air sample comprises air exhaled by a patient.

4. The method according to claim 1, wherein the air sample comprises air from a resuscitator.

5. The method according to claim 1, wherein the air sample comprise air from an endotracheal tube.

6. The method according to claim 1, wherein determining the color of the indicator solution occurs between approximately 5 and 20 seconds after exposing the carbon dioxide detector to the air sample.

7. The method according to claim 1, wherein a color of the indicator solution indicates a carbon dioxide concentration of less than approximately 0.5% in the air sample.

8. The method according to claim 1, wherein a color of the indicator solution indicates a carbon dioxide concentration of at least approximately 2% in the air sample.

9. The method according to claim 1, wherein a color of the indicator solution indicates a carbon dioxide concentration of between approximately 0.5% and 2% in the air sample.

10. A method of detecting carbon dioxide in a breath-to-breath manner comprising:
attaching to a subject a carbon dioxide detector having:
a borosilicate substrate having an acrylic binder; and
a carbon dioxide responsive indicator solution disposed on the borosilicate substrate; and
determining whether carbon dioxide is present in respired air during at least every breath of the subject in a time interval.

11. The method of detecting carbon dioxide according to claim 10, wherein the time interval ranges from approximately 1 second to approximately 20 seconds.

12. The method of detecting carbon dioxide according to claim 10, wherein the time interval ranges from approximately 3 seconds to approximately 6 seconds.

13. The method of detecting carbon dioxide according to claim 10, wherein the interval is approximately 5 seconds.

14. A method of detecting carbon dioxide comprising:
providing an air sample to a carbon dioxide detector having:
a borosilicate substrate having an acrylic binder; and
a carbon dioxide responsive indicator solution disposed on the borosilicate substrate; and
measuring the carbon dioxide in the air sample, wherein the indicator responds to the carbon dioxide in a time interval ranging from approximately 1 second to 20 seconds.

15. The method of detecting carbon dioxide according to claim 14, wherein the time interval ranges from approximately 1 to approximately 5 seconds.

16. A method for determining whether a gaseous sample contains a concentration of carbon dioxide, comprising:
contacting the gaseous sample with a carbon dioxide detector having a carbon dioxide sensitive indicator disposed on a borosilicate substrate to detect carbon dioxide in the gaseous sample and wherein the borosilicate substrate comprises an acrylic binder.

17. The method according to claim 16, wherein contacting occurs for a diagnostically effective period of time.

18. The method according to claim 16, comprising:
   replacing the gaseous sample with the second gaseous sample; and
   contacting the second gaseous sample with the carbon dioxide detector to detect carbon dioxide in the second gaseous sample.

19. The method of claim 1, wherein a color of the indicator solution indicates a carbon dioxide concentration greater than 5%.

20. The method of claim 1, wherein the indicator solution includes four colors, the first color indicates a carbon dioxide concentration of less than approximately 0.5% in the air sample, the second color indicates a carbon dioxide concentration of between approximately 0.5% to 2% in the air sample; the third color indicates a carbon dioxide concentration of between approximately 2% to 5% in the air sample; and the fourth color indicates a carbon dioxide concentration of greater than approximately 5% in the air sample.

* * * * *